(12) United States Patent
Kim et al.

(10) Patent No.: US 10,752,659 B2
(45) Date of Patent: Aug. 25, 2020

(54) RHTB PROTEIN VARIANTS AND THE METHOD OF PRODUCING O-PHOSPHOSERINE USING THE SAME

(71) Applicant: CJ CHEILJEDANG CORPORATION, Seoul (KR)

(72) Inventors: Sol Kim, Gyeonggi-do (KR); Hye Won Kim, Gyeonggi-do (KR); Jin Sook Chang, Seoul (KR); In Hwa Yoo, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/423,986

(22) Filed: May 28, 2019

(65) Prior Publication Data

US 2019/0284247 A1    Sep. 19, 2019

Related U.S. Application Data

(62) Division of application No. 15/679,671, filed on Aug. 17, 2017, now Pat. No. 10,344,059, which is a (Continued)

(30) Foreign Application Priority Data

May 10, 2013    (KR) .......................... 10-2013-0053428

(51) Int. Cl.
*C12N 15/63*    (2006.01)
*C12N 15/52*    (2006.01)
(Continued)

(52) U.S. Cl.
CPC .......... *C07K 14/245* (2013.01); *C12N 9/0006* (2013.01); *C12N 9/1096* (2013.01);
(Continued)

(58) Field of Classification Search
CPC ........ C12P 13/005; C12P 13/12; C12N 15/52; C12N 15/63; C12N 9/0006; C12N 9/1096; C12N 9/16
See application file for complete search history.

(56) References Cited

U.S. PATENT DOCUMENTS 9,765,124 B2    9/2017 Kim et al.
10,125,179 B2    11/2018 Kim et al.
(Continued)

FOREIGN PATENT DOCUMENTS

EP    0885962 B1    4/2005
EP    2444481 A1    4/2012
(Continued)

OTHER PUBLICATIONS

GenBank Accession No. U000962, "*Escherichia coli* str. K-12 substr. MG1655, complete genome," two pages, dated Feb. 26, 2013.
(Continued)

*Primary Examiner* — Padmavathi Baskar
(74) *Attorney, Agent, or Firm* — Cooley LLP

(57) ABSTRACT

The present invention relates to an RhtB (homoserine/homoserine lactone export transporter) protein variant having an enhanced ability to export O-phosphoserine (OPS) that is a precursor of L-cysteine, a polynucleotide encoding the protein, a vector comprising the polynucleotide, an OPS-producing microorganism comprising the protein variant, a method of producing O-phosphoserine using the microorganism, and a method for preparing cysteine or its derivatives, which comprises reacting O-phosphoserine, produced by the method above, with a sulfide in the presence of O-phosphoserine sulfhydrylase (OPSS) or a microorganism that expresses OPSS.

4 Claims, 1 Drawing Sheet

Specification includes a Sequence Listing.

Related U.S. Application Data division of application No. 14/890,422, filed as application No. PCT/KR2014/004150 on May 9, 2014, now Pat. No. 9,765,124.

(51) Int. Cl.

| | | |
|---|---|---|
| *C12N 9/16* | (2006.01) | |
| *C12N 9/00* | (2006.01) | |
| *C07K 14/245* | (2006.01) | |
| *C12P 13/12* | (2006.01) | |
| *C12P 13/06* | (2006.01) | |
| *C12N 9/04* | (2006.01) | |
| *C12N 9/10* | (2006.01) | |
| *C12P 13/00* | (2006.01) | |

(52) U.S. Cl.
CPC .............. *C12N 9/16* (2013.01); *C12N 15/52* (2013.01); *C12N 15/63* (2013.01); *C12P 13/005* (2013.01); *C12P 13/06* (2013.01); *C12P 13/12* (2013.01)

(56) References Cited

U.S. PATENT DOCUMENTS

| | | | |
|---|---|---|---|
| 10,344,059 B2 * | 7/2019 | Kim | ............ C12P 13/12 |
| 2012/0190081 A1 | 7/2012 | Chang et al. | |

FOREIGN PATENT DOCUMENTS

| | | |
|---|---|---|
| KR | 10-2012-0041073 A | 4/2012 |
| KR | 10-2012-0041115 A | 4/2012 |

OTHER PUBLICATIONS

NCBI! Reference Sequence: ZP_07143650,1, "YGGT family protein [*Escherichia coli* MS 187-1]," two pages, dated Nov. 27, 2012.

Franke et al., "YfiK from *Escherichia coil* Promotes Export of O-Acetylserine and Cysteine," J. Bacteriol. 185(4): 1161-1166, Feb. 2003.

Korean intellectual Property Office, International Search Report for International Application No. PCT/KR2014/004150, dated Aug. 27, 2014, four pages.

NCBI Reference Sequence: WP_001466488.1, "homoserine/homoserine lactone efflux protein [*Escherichia coil*]," accessed May 3, 2013.

Ryu et al., "Continuous L-Cysteine production using immobilized cell reactors and product extractors," Process Biochemistry 32(3): 201-209, 1997.

Wada and Takagi, "Metabolic pathways and biotechnological production of L-Cysteine" Appl. Microbiol. Biotechnol. 73:48-54, 2006.

Westrop et al., "Cysteine biosynthesis in Trichomonas vaginalis involves cysteine synthase utilizing O-phosphoserine," J. Biol. Chem. 281(35): 25062-25075, Sep. 1, 2006.

Zakataeva et al., "The novel transmembrane *Escherichia coli* proteins involved in the amino acid reflux," FEBS Letters 452: 228-232, 1999.

* cited by examiner

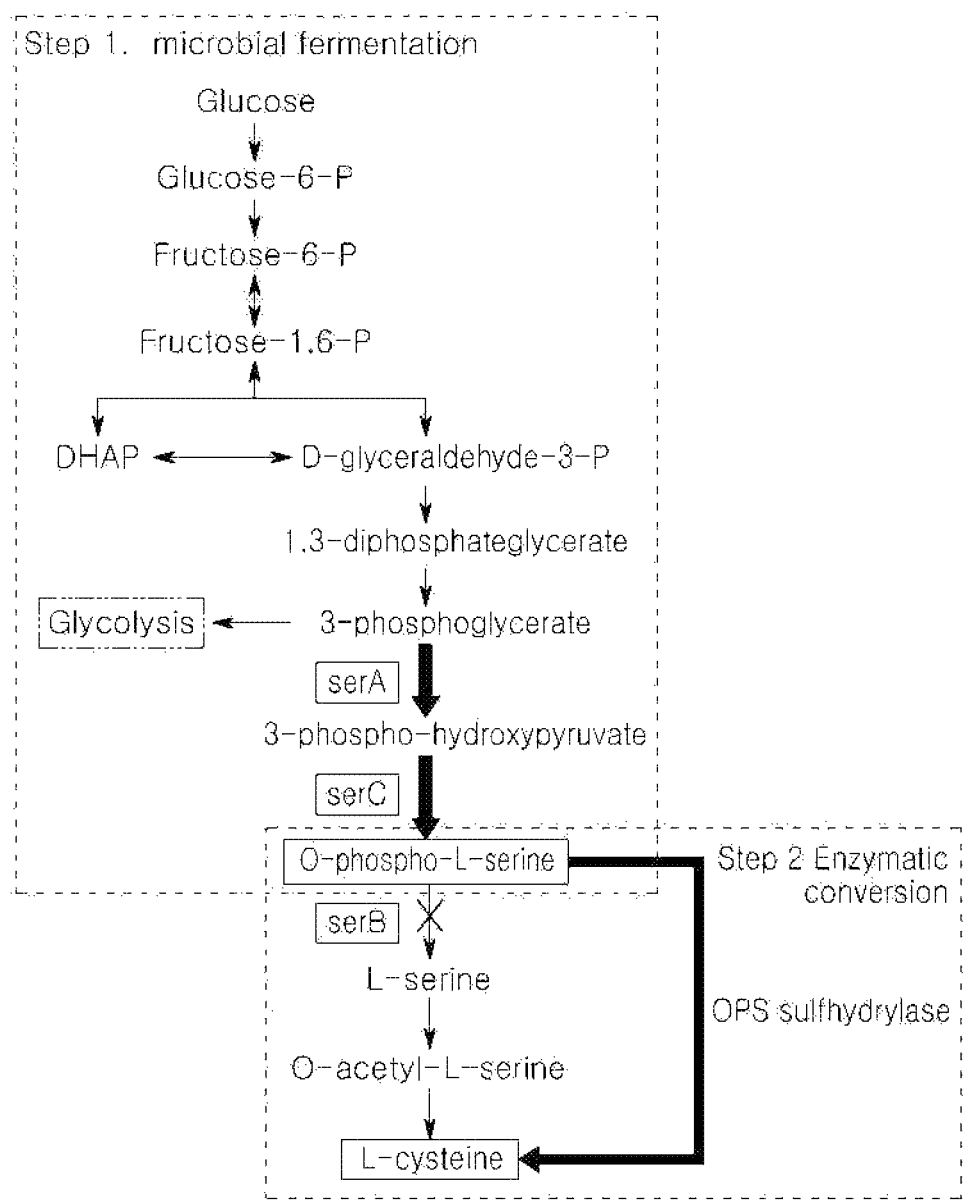

SEQUENCE LISTING

<160> NUMBER OF SEQ ID NOS: 9

<210> SEQ ID NO 1
<211> LENGTH: 206
<212> TYPE: PRT
<213> ORGANISM: Escherichia coli
<220> FEATURE:
<221> NAME/KEY: PEPTIDE
<222> LOCATION: (1)..(206)
<223> OTHER INFORMATION: rhtB (homoserine / homoserine lactone efflux transporter)

<400> SEQUENCE: 1

```
Met Thr Leu Glu Trp Trp Phe Ala Tyr Leu Leu Thr Ser Ile Ile Leu
1               5                   10                  15

Ser Leu Ser Pro Gly Ser Gly Ala Ile Asn Thr Met Thr Thr Ser Leu
            20                  25                  30

Asn His Gly Tyr Arg Gly Ala Val Ala Ser Ile Ala Gly Leu Gln Thr
        35                  40                  45

Gly Leu Ala Ile His Ile Val Leu Val Gly Val Gly Leu Gly Thr Leu
    50                  55                  60

Phe Ser Arg Ser Val Ile Ala Phe Glu Val Leu Lys Trp Ala Gly Ala
65                  70                  75                  80

Ala Tyr Leu Ile Trp Leu Gly Ile Gln Gln Trp Arg Ala Ala Gly Ala
                85                  90                  95

Ile Asp Leu Lys Ser Leu Ala Ser Thr Gln Ser Arg Arg His Leu Phe
            100                 105                 110

Gln Arg Ala Val Phe Val Asn Leu Thr Asn Pro Lys Ser Ile Val Phe
        115                 120                 125

Leu Ala Ala Leu Phe Pro Gln Phe Ile Met Pro Gln Gln Pro Gln Leu
    130                 135                 140

Met Gln Tyr Ile Val Leu Gly Val Thr Thr Ile Val Val Asp Ile Ile
145                 150                 155                 160

Val Met Ile Gly Tyr Ala Thr Leu Ala Gln Arg Ile Ala Leu Trp Ile
                165                 170                 175

Lys Gly Pro Lys Gln Met Lys Ala Leu Asn Lys Ile Phe Gly Ser Leu
            180                 185                 190

Phe Met Leu Val Gly Ala Leu Leu Ala Ser Ala Arg His Ala
    195                 200                 205
```

<210> SEQ ID NO 2
<211> LENGTH: 206
<212> TYPE: PRT
<213> ORGANISM: Escherichia coli
<220> FEATURE:
<221> NAME/KEY: PEPTIDE
<222> LOCATION: (1)..(206)
<223> OTHER INFORMATION: rhtB (homoserine / homoserine lactone efflux transporter) m1

<400> SEQUENCE: 2

```
Met Thr Leu Glu Trp Trp Phe Ala Tyr Leu Met Thr Ser Ile Ile Leu
1               5                   10                  15

Ser Leu Ser Pro Gly Ser Gly Ala Ile Asn Thr Met Thr Thr Ser Leu
            20                  25                  30

Asn His Gly Tyr Arg Gly Ala Val Ala Ser Ile Ala Gly Leu Gln Thr
        35                  40                  45

Gly Leu Ala Ile His Ile Ala Leu Val Gly Val Gly Leu Gly Thr Leu
    50                  55                  60
```

-continued

```
Phe Ser Arg Ser Val Ile Ala Phe Glu Val Leu Lys Trp Ala Gly Ala
 65                  70                  75                  80

Ala Tyr Leu Ile Trp Leu Gly Ile Gln Gln Trp Arg Ala Ala Gly Ala
                 85                  90                  95

Ile Asp Leu Lys Ser Leu Ala Ser Thr Gln Ser Arg Arg His Leu Phe
            100                 105                 110

Gln Arg Ala Val Phe Val Asn Leu Thr Asn Pro Lys Ser Ile Val Phe
        115                 120                 125

Leu Ala Ala Leu Phe Pro Gln Phe Ile Met Pro Gln Gln Pro Gln Leu
    130                 135                 140

Met Gln Tyr Ile Val Leu Gly Val Thr Thr Ile Val Val Asp Ile Ile
145                 150                 155                 160

Val Met Ile Gly Tyr Ala Thr Leu Ala Gln Arg Ile Ala Leu Trp Ile
                165                 170                 175

Lys Gly Pro Lys Gln Met Lys Ala Leu Asn Lys Ile Phe Gly Ser Leu
            180                 185                 190

Phe Met Leu Val Gly Ala Leu Leu Ala Ser Ala Arg His Ala
        195                 200                 205
```

<210> SEQ ID NO 3
<211> LENGTH: 206
<212> TYPE: PRT
<213> ORGANISM: Escherichia coli
<220> FEATURE:
<221> NAME/KEY: PEPTIDE
<222> LOCATION: (1)..(206)
<223> OTHER INFORMATION: rhtB (homoserine / homoserine lactone efflux transporter) m2

<400> SEQUENCE: 3

```
Met Thr Leu Glu Trp Trp Phe Ala Tyr Leu Leu Thr Ser Ile Ile Leu
  1               5                  10                  15

Ser Leu Ser Pro Gly Ser Gly Ala Ile Asn Thr Met Thr Thr Ser Leu
                 20                  25                  30

Asn His Gly Tyr Arg Gly Ala Val Ala Ser Ile Ala Gly Leu Gln Thr
             35                  40                  45

Gly Leu Ala Ile His Met Val Leu Val Gly Val Gly Leu Gly Thr Leu
         50                  55                  60

Phe Ser Arg Ser Val Ile Ala Phe Glu Val Leu Lys Trp Ala Gly Ala
 65                  70                  75                  80

Ala Tyr Leu Ile Trp Leu Gly Ile Gln Gln Trp Arg Ala Ala Gly Ala
                 85                  90                  95

Ile Asp Leu Lys Ser Leu Ala Ser Thr Gln Ser Arg Arg His Leu Phe
            100                 105                 110

Gln Arg Ala Val Phe Val Asn Leu Thr Asn Pro Lys Ser Ile Val Phe
        115                 120                 125

Leu Ala Ala Leu Phe Pro Gln Phe Ile Met Pro Gln Gln Pro Gln Leu
    130                 135                 140

Met Gln Tyr Ile Val Leu Gly Val Thr Thr Ile Val Val Asp Ile Thr
145                 150                 155                 160

Val Met Ile Gly Tyr Ala Thr Leu Ala Gln Arg Ile Ala Leu Trp Ile
                165                 170                 175

Lys Gly Pro Lys Gln Met Lys Ala Leu Asn Lys Ile Phe Gly Ser Leu
            180                 185                 190

Phe Met Leu Val Gly Ala Leu Leu Ala Ser Ala Arg His Ala
        195                 200                 205
```

<210> SEQ ID NO 4
<211> LENGTH: 206
<212> TYPE: PRT
<213> ORGANISM: Escherichia coli
<220> FEATURE:
<221> NAME/KEY: PEPTIDE
<222> LOCATION: (1)..(206)
<223> OTHER INFORMATION: rhtB (homoserine / homoserine lactone efflux transporter) m3

<400> SEQUENCE: 4

Met Thr Leu Glu Trp Trp Phe Ala Tyr Leu Leu Thr Ser Ile Ile Leu
1               5                   10                  15

Ser Leu Ser Pro Gly Ser Gly Ala Ile Asn Thr Met Thr Thr Ser Leu
            20                  25                  30

Asn His Gly Tyr Arg Gly Ala Val Ala Ser Ile Ala Gly Leu Gln Thr
        35                  40                  45

Gly Leu Ala Ile His Ile Val Leu Val Gly Val Gly Leu Gly Thr Leu
    50                  55                  60

Phe Ser Arg Ser Val Ile Ala Phe Glu Val Leu Lys Trp Ala Gly Ala
65                  70                  75                  80

Ala Tyr Leu Ile Trp Leu Gly Ile Gln Gln Trp Arg Ala Ala Gly Ala
                85                  90                  95

Ile Asp Leu Lys Ser Leu Ala Ser Thr Gln Ser Arg Arg His Leu Phe
            100                 105                 110

Gln Arg Ala Val Leu Val Asn Leu Thr Asn Pro Lys Ser Ile Val Phe
        115                 120                 125

Leu Ala Ala Leu Phe Pro Gln Phe Ile Met Pro Gln Gln Pro Gln Leu
    130                 135                 140

Met Gln Tyr Ile Val Leu Gly Val Thr Thr Ile Val Val Asp Ile Thr
145                 150                 155                 160

Val Met Ile Gly Tyr Ala Pro Pro Ala Gln Arg Ile Ala Leu Trp Ile
                165                 170                 175

Lys Gly Pro Lys Gln Met Arg Ala Leu Asn Lys Ile Phe Gly Ser Leu
            180                 185                 190

Phe Met Leu Val Gly Ala Leu Leu Ala Ser Ala Arg His Ala
        195                 200                 205

<210> SEQ ID NO 5
<211> LENGTH: 206
<212> TYPE: PRT
<213> ORGANISM: Escherichia coli
<220> FEATURE:
<221> NAME/KEY: PEPTIDE
<222> LOCATION: (1)..(206)
<223> OTHER INFORMATION: rhtB (homoserine / homoserine lactone efflux transporter) m4

<400> SEQUENCE: 5

Met Thr Leu Glu Trp Trp Phe Ala Tyr Leu Leu Thr Ser Ile Ile Leu
1               5                   10                  15

Ser Leu Ser Pro Gly Ser Gly Ala Ile Asn Ala Met Thr Thr Ser Leu
            20                  25                  30

Asn His Gly Tyr Arg Gly Ala Val Ala Ser Ile Ala Gly Leu Gln Thr
        35                  40                  45

Gly Leu Ala Ile His Ile Val Leu Val Gly Val Gly Leu Gly Thr Leu
    50                  55                  60

Phe Ser Arg Ser Val Ile Ala Phe Glu Val Leu Lys Trp Ala Gly Ala
65                  70                  75                  80

```
Ala Tyr Met Ile Trp Leu Gly Ile Gln Gln Trp Arg Ala Gly Ala
                85                  90                  95

Ile Asp Leu Lys Ser Leu Ala Ser Thr Gln Ser Arg Arg His Leu Phe
           100                 105                 110

Gln Arg Ala Val Phe Val Asn Leu Thr Asn Pro Lys Ser Ile Val Phe
           115                 120                 125

Leu Ala Ala Leu Phe Pro Gln Phe Ile Met Pro Gln Gln Pro Gln Pro
       130                 135                 140

Met Gln Tyr Ile Val Leu Gly Val Thr Thr Ile Val Val Asp Ile Ile
145                 150                 155                 160

Glu Met Ile Gly Tyr Ala Thr Leu Ala Gln Arg Ile Ala Leu Trp Ile
               165                 170                 175

Lys Gly Pro Lys Gln Met Lys Ala Leu Asn Lys Ile Phe Gly Ser Leu
           180                 185                 190

Phe Met Leu Val Gly Ala Leu Leu Ala Ser Ala Arg His Ala
       195                 200                 205
```

<210> SEQ ID NO 6
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      construct pCL-Prmf-serA(G336V)-serC_Prmf-genes

<400> SEQUENCE: 6
aagcttcggg cctcttcgct attacgc                                   27

<210> SEQ ID NO 7
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      construct pCL-Prmf-serA(G336V)-serC_Prmf-genes

<400> SEQUENCE: 7
aagcttaggc ttacccgtct tactgtc                                   27

<210> SEQ ID NO 8
<211> LENGTH: 26
<212> TYPE: DNA
<213> ORGANISM: Artificial Sequence
<220> FEATURE:
<223> OTHER INFORMATION: primer for amplification of rhtB to construct
      pCL-Prmf-rhtB

<400> SEQUENCE: 8
gcgatatcat gaccttagaa tggtgg                                    26

<210> SEQ ID NO 9
<211> LENGTH: 23
<212> TYPE: DNA
<213> ORGANISM: Artificial Sequence
<220> FEATURE:
<223> OTHER INFORMATION: primer for amplification of rhtB to construct
      pCL-Prmf-rhtB

<400> SEQUENCE: 9
gctctagatc acgcatgcct cgc                                       23

RHTB PROTEIN VARIANTS AND THE METHOD OF PRODUCING O-PHOSPHOSERINE USING THE SAME

CROSS-REFERENCES TO RELATED APPLICATIONS

This application is a Divisional of U.S. application Ser. No. 15/679,671, filed Aug. 17, 2017, now allowed, which is a Divisional of U.S. application Ser. No. 14/890,422, now issued U.S. Pat. No. 9,765,124, which is the National Stage of International Application No. PCT/KR2014/004150, filed May 9, 2014, which claims priority to Korean Patent Application No. 10-2013-0053428, filed May 10, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_038_05US_ST25.txt. The text file is 11 KB, created on May 28, 2019, and is being submitted electronically via EFS-Web.

BACKGROUND OF THE INVENTION

Field of the Invention

The present invention relates to an RhtB (homoserine/homoserine lactone export transporter) protein variant having an enhanced ability to export O-phosphoserine (OPS) that is a precursor of L-cysteine, a polynucleotide encoding the protein, a vector comprising the polynucleotide, an OPS-producing microorganism comprising the protein variant, a method of producing O-phosphoserine using the microorganism, and a method for preparing cysteine or its derivatives, which comprises reacting O-phosphoserine, produced by the OPS-producing method, with a sulfide in the presence of O-phosphoserine sulfhydrylase (OPSS) or a microorganism that expresses OPSS.

Description of the Prior Art

L-cysteine, an amino acid playing an important role in the metabolism of sulfur in all living organisms, is used not only in the synthesis of biological proteins such as hair keratin, glutathione, biotin, methionine, and other sulfur-containing metabolites, but also as a precursor for biosynthesis of coenzyme A.

Known methods of producing L-cysteine using microorganisms include a method of biologically converting D,L-ATC to L-cysteine using microorganisms (Ryu OH et al., Process Biochem., 32:201-209, 1997). Another known method is a method of producing L-cysteine by direct fermentation using *E. coli* (EP 0885962B; Wada M and Takagi H, Appl. Microbiol. Biochem., 73:48-54, 2006). Meanwhile, the present inventors found an enzyme (O-phosphoserine sulfhydrylase (OPSS)) that synthesizes L-cysteine from O-phosphoserine (OPS) in certain microorganisms. Based on this finding, the present inventors developed a method of producing cysteine by reacting OPS with the OPSS enzyme by culturing a mutated microorganism to accumulate OPS therein (Korean Patent Laid-Open Publication No. 10-2012-004111). The needs still exist to produce OPS in excessive amounts in order to produce cysteine at high yield. Accordingly, the present inventors have made extensive efforts to discover an appropriate exporter that enables O-phosphoserine produced in an OPS-producing strain to be released from the cells smoothly. In addition, based on various kinds of known transporters, the present inventors screened ydeD encoding O-acetylserine/cysteine efflux protein, yfiK encoding O-acetylserine/cysteine export permease (Franke I, Resch A, Dassler T, Maier T and Bock A, J. Bacteriology, 185: 1161-166, 2003), rhtB encoding homoserine/homoserine lactone efflux protein (Zakataeva NP, Aleshin VV, Tokmakova IL, Troshin PV, Livshits VA FEBS Lett 1999; 452(3); 228-32) and the like, and particularly found that the enhancement of RhtB in the OPS-producing strain results in an increase in the concentration of OPS (Korean Patent Laid-Open Publication No. 10-2012-0041115). However, for the production of higher yield of cysteine, the development of a transporter having a higher ability to export a precursor OPS from the OPS-producing strain is still required.

SUMMARY OF THE INVENTION

The present inventors have made extensive efforts to discover RhtB protein variants having increased OPS export activity so as to be able to further increase the production of OPS, and as a result, have identified four novel RhtB protein variants having increased OPS export activity, and have found that the proteins can export OPS from an OPS-producing strain more effectively, thereby completing the present invention.

It is an object of the present invention to provide an RhtB (homoserine/homoserine lactone export transporter) protein variant having enhanced O-phosphoserine (OPS) export activity.

Another object of the present invention is to provide a polynucleotide encoding the protein variant and a vector comprising the polynucleotide.

Still another object of the present invention is to provide an OPS-producing microorganism comprising the protein variant.

Still another object of the present invention is to provide a method for producing OPS, comprising culturing the microorganism.

Still another object of the present invention is to provide a method for producing cysteine or its derivatives, comprising reacting O-phosphoserine, produced by the above-described method for producing O-phosphoserine, with a sulfide in the presence of O-phosphoserine sulfhydrylase (OPSS) or a microorganism that expresses OPSS.

BRIEF DESCRIPTION OF THE DRAWINGS

FIG. 1 is a schematic diagram showing a method of producing L-cysteine by accumulating O-phosphoserine from the biosynthesis and microbial fermentation of O-phosphoserine and enzymatically converting the accumulated O-phosphoserine to L-cysteine.

DETAILED DESCRIPTION OF THE INVENTION

Apsect of the present invention include an RhtB (homoserine/homoserine lactone export transporter) protein variant having enhanced O-phosphoserine (OPS) export activity.

As used herein, the term "O-phosphoserine (hereinafter described as "OPS")" refers to an ester of serine and phosphoric acid, that is a component of many proteins. The OPS is a precursor of L-cysteine and can be converted to cysteine by reaction with a sulfide under the catalytic action of OPS sulfhydrylase(hereinafter described as "OPSS"). Accordingly, it is an important factor for increasing productivity of OPS in the production of cysteine, and thus it is required to develop transporters that enable intracellular OPS to be effectively secreted from OPS-producing strains.

As used herein, the term "RhtB (homoserine/homoserine lactone export transporter) protein" is known as an exporter of the homoserine/homoserine lactone that is a precursor of threonine. Information about the RhtB protein is available from known databases such as the NCBI GenBank. For example, it may be a protein deposited under the accession number AAT48223 (EG11469), and the amino acid sequence thereof may be set forth in SEQ ID NO: 1.

As used herein, the expression "RhtB (homoserine/homoserine lactone export transporter) protein variant having enhanced O-phosphoserine exporting activity" refers to a protein which has enhanced OPS export activity compared to wild-type RhtB protein and which comprises a mutation in one or more amino acids of the amino acid sequence of wild-type RhtB protein. Specifically four RhtB protein variants having enhanced OPS export activity are identified by inducing random mutations in a polynucleotide coding the RhtB protein. Among the identified protein variants, a protein variant having an amino acid sequence of SEQ ID NO: 2 was labeled "RhtB m1"; an RhtB protein variant having an amino acid sequence of SEQ ID NO: 3 was labeled "RhtB m2"; an RhtB protein variant having an amino acid sequence of SEQ ID NO: 4 was labeled "RhtB m3"; and an RhtB protein variant having an amino acid sequence of SEQ ID NO: 5 was labeled "RhtB m4".

The RhtB protein variants of the present invention include not only the proteins having an amino acid sequence as set forth in SEQ ID NO: 2, 3, 4 or 5, but also proteins that have an amino acid sequence showing a homology of at least 70%, specifically at least 80%, more specifically at least 90%, even more specifically at least 95%, still even more specifically at least 98%, and most specifically at least 99% to the amino acid sequences of SEQ ID NO: 2, 3, 4 or 5, and have substantially enhanced O-phosphoserine export activity compared to a wild-type RhtB protein. In addition, it is obvious that proteins comprising a deletion, modification, substitution or addition of one or more amino acids of the amino acid sequence of the RhtB protein are also included in the scope of the present invention, as long as they comprise an amino acid sequence having the above-described homology and have biological activity substantially identical or comparable to the RhtB protein.

As used herein, the term "homology" refers to the percentage of identity between two polynucleotide or polypeptide moieties. The correspondence between the sequences from one form to another can be determined by techniques known in the art. For example, homology can be determined by a direct comparison of the sequence information between two polypeptide molecules or polynucleotide molecules by aligning the sequence information and using readily available computer programs. Alternatively, homology can be determined by hybridization of polynucleotides under conditions which form stable duplexes between homologous regions, followed by digestion with single-stranded-specific nuclease, and size determination of the digested fragments.

As used herein, the term "homologous" in all its grammatical forms and spelling variations refers to the relationship between proteins that possess a "common evolutionary origin," including proteins from superfamilies and homologous proteins from different species. Such proteins (and their encoding genes) have sequence homology, as reflected by their high degree of sequence similarity. However, in common usage and in the present invention, the term "homologous," when modified with an adjective such as "very high," may refer to sequence similarity and not a common evolutionary origin.

As used herein, the term "sequence similarity" refers to the degree of identity or correspondence between nucleic acid or amino acid sequences of proteins that may or may not share a common evolutionary origin. In one embodiment, two amino acid sequences are "substantially homologous" or "substantially similar" when at least about 21% (specifically at least about 50%, and most specifically at least about 75%, 90%, 95%, 96%, 97% or 99%) of the polypeptide match over the defined length of the amino acid sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see, e.g., Sambrook et al., 1989, infra).

Because the RhtB protein variants of the present invention have enhanced OPS export activity compared to a wild-type RhtB protein, the OPS productivity of an OPS-producing microorganism can be increased by expressing the RhtB protein variants of the present invention in the microorganism.

In an example of the present invention, in order to identify RhtB protein variants having enhanced OPS export activity, the gene encoding the wild-type RhtB protein was randomly mutated, and the mutated gene was introduced into recombinant E. coli microorganisms having reduced activity of endogenous phosphoserine phosphatase (hereinafter described as "SerB"), and colonies showing the removal of growth inhibition under the medium conditions containing an excessive amount of OPS, thereby identifying 4 kinds of RhtB protein variants as described above (Example 1). Also, an OPS-producing strain, which expresses the RhtB protein variant of the present invention and has reduced activity of endogenous SerB, showed an increase in OPS productivity of up to 10% compared to an OPS-producing strain expressing the wild-type RhtB protein, and a strain which expresses the RhtB protein variant and has enhanced activities of SerA and SerC showed an increase in OPS productivity of up to 14% (Example 2). Such results suggest that the RhtB protein variant of the present invention in an OPS-producing strain can significantly increase the OPS productivity of the strain.

A further aspect of the present invention also includes a polynucleotide encoding the RhtB protein variant and a vector comprising the polynucleotide.

As used herein, the term "polynucleotide" refers to a polymer of nucleotide units linked to each other by a covalent bond to form a chain. The term generally means a DNA or RNA strand having any length. In the present invention, the term means a polynucleotide fragment encoding the RhtB protein variant.

As used herein, the term "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" may include both viral and nonviral vehicles for introducing the nucleic acid into a host cell in vitro, ex vivo or in vivo. It may also include minicircle DNAs. For example, the vector may be a plasmid without bacterial DNA sequences. The removal of bacterial DNA sequences which are rich in CpG regions has been shown to decrease transgene expression silencing and result in more persistent expression from plasmid DNA vectors (e.g., Ehrhardt, A. et al. (2003) HumGene Ther 10: 215-25; Yet, N. S. (2002) MoI Ther 5: 731-38; Chen, Z. Y. et al. (2004) Gene Ther 11:856-64). The term "vector" may also include transposons (Annu Rev Genet. 2003;37:3-29), or artificial chromosomes. Specifically, vectors such as pACYC177, pACYC184, pCL1920, pECCG117, pUC19, pBR322 and pMW118 may be used and in an example of the present invention, a pCL1920 vector was used.

A further aspect of the present invention also includes an OPS-producing microorganism comprising the RhtB protein variant.

Herein, the RhtB protein, the RhtB protein variant and the OPS are as described above.

The OPS-producing microorganism comprising the RhtB protein variant of an example of the present invention may effectively secrete OPS compared to a microorganism comprising the wild-type RhtB protein, and thus it can be more useful for the production of OPS that is a precursor of cysteine.

The OPS-producing microorganism comprising the RhtB protein variant having enhanced OPS export activity may be a microorganism comprising the RhtB protein variant, which has enhanced OPS export activity due to a mutation in the chromosomal gene encoding the RhtB protein, and/or a microorganism which comprises the RhtB protein variant having enhanced OPS export activity and is obtained by introducing a vector comprising a polynucleotide encoding the RhtB protein variant, but the scope of the present invention is not limited thereto. In an example of the present invention, an OPS-producing microorganism comprising a representative RhtB protein variant having enhanced OPS export activity may be constructed by introducing into *E. coli* a vector comprising a polynucleotide encoding the RhtB protein variant having enhanced OPS export activity.

Further, the OPS-producing microorganism comprising the RhtB protein variant may have enhanced activity of the RhtB protein variant.

Methods for enhancing the activity of the RhtB protein include, but are not limited to, a method of increasing the intracellular copy number of a gene encoding the protein variant, a method of introducing a mutation into an expression regulatory sequence for the chromosomal gene encoding the protein variant, a method of replacing the expression regulatory sequence for the chromosomal gene encoding the protein variant with a sequence having strong activity, a method of substituting the chromosomal gene encoding the protein with a gene mutated to increase the activity of the protein variant, and a method of introducing a mutation into the chromosomal gene encoding the protein to enhance the activity of the protein. The method of enhancing the activity of the protein can likewise be applied to enhance the activities of other proteins.

As used herein, the team "introduction" refers to a method of transferring a vector, which comprises a polynucleotide encoding the RhtB protein variant, to a host cell. This introduction may be easily performed using any conventional method known in the art. In general, examples of the introduction method may include $CaCl_2$ precipitation, the Hanahan method that is an improved $CaCl_2$ method that uses DMSO (dimethyl sulfoxide) as a reducing material to increase efficiency, electroporation, calcium phosphate precipitation, protoplast fusion, agitation using silicon carbide fiber, Agrobacterium-mediated transformation, PEG-mediated transformation, dextran sulfate-mediated transformation, lipofectamine-mediated transformation, and desiccation/inhibition-mediated transformation. The method for transforming the vector is not limited to the above-described examples, and any conventional transformation or transfection methods known in the art may be used without limitation.

As used herein, the term "OPS-producing microorganism" refers to a prokaryotic or eukaryotic microbial strain capable of producing OPS therein. For example, the OPS-producing microorganism may be a microorganism capable of accumulating OPS therein by genetic engineering, but is not limited thereto. For the purpose of the present invention, the microorganism may be any prokaryotic or eukaryotic microorganism that comprises the RhtB protein variant, and thus can produce OPS. Examples of the microorganism include microbial strains belonging to the genus *Escherichia*, the genus *Erwinia*, the genus *Serratia*, the genus *Providencia*, the genus *Corynebacterium* and the genus *Brevibacterium*. Specifically, the microorganism may be a microorganism of the genus *Escherichia*. More specifically, it may be *E. coli*. Particularly, a microorganism of the *Escherichia* or the genus *Corynebacterium* can produce OPS and L-serine, because it contains SerA, SerC and SerB proteins that are enzymes in the biosynthesis pathway of L-serine (Ahmed Zahoor, Computational and structural biotechnology journal, vol 3, 2012 october; Wendisch VF et al., Curr Opin Microbiol. 2006 June;9(3):268-74; Peters-Wendisch P et al., Appl Environ Microbiol. 2005 November;71 (11):7139-44).

The OPS-producing microorganism may be specifically a microorganism mutated to reduce the activity of endogenous phosphoserine phosphatase (SerB). The SerB has an activity of converting OPS to L-serine, and thus the microorganism mutated to reduce the SerB activity may have the property of accumulating OPS therein, suggesting that it is useful for the production of OPS. The reduction in the activity of SerB means that the activity of SerB is reduced or is removed compared to that in a non-mutated strain. The reduction in the activity of SerB can be achieved using various methods well known in the art. Examples of the method for reducing the activity of the SerB enzyme include, but are not limited to, a method of substituting the chromosomal gene encoding the enzyme with a gene mutated to reduce or remove the activity of the enzyme, a method of introducing a mutation into an expression regulatory sequence for the chromosomal gene encoding the enzyme, a method of replacing an expression regulatory sequence for the chromosomal gene encoding the enzyme with a gene having weak activity, deleting the chromosomal gene encoding the enzyme, a method of introducing an antisense oligonucleotide that binds complementarily to the transcript of the chromosomal gene to inhibit the translation of the mRNA into the protein, a method of artificially adding a sequence complementary to the SD sequence of the gene encoding the enzyme in the front of the SD sequence to form a secondary structure that makes the adhesion of ribosome impossible, and a reverse transcription engineering (RTE) method of adding a promoter to the 3' end of the open reading frame (ORF) of the corresponding sequence so as to be reverse-transcribed. In an example of the present invention, using CA07-0012 (accession number: KCCM11121P) disclosed in Korean Patent Laid-Open Publication No. 10-2012-004115 and US Patent Laid-Open Publication No. 2012-0190081 as a microorganism mutated to reduce the activity of endogenous SerB, a vector comprising a polynucleotide encoding the RhtB protein variant of the present invention was introduced into the microorganism.

Further, the OPS-producing microorganism may be a microorganism having enhanced activity of phosphoglycerate dehydrogenase (SerA) or phosphoserine aminotransferase (SerC).

The SerA is a protein having an activity of converting 3-phosphoglycerate to 3-phosphohydroxypyruvate, and the SerA may be a wild-type protein or a mutant resistant to serine feedback inhibition. Also, the SerC is a protein having an activity of converting 3-phosphoglycerate to O-phosphoserine. Thus, the microorganism with enhanced activity of SerA and/or SerC may be useful as an OPS-producing strain. In an example of the present invention, using CA07-0022/pCL-Prmf-serA*(G336V)-serC (accession number: KCCM11103P), which is a microorganism having enhanced activity of SerA (resistant to serine feedback inhibition) and SerC as disclosed in Korean Patent Laid-Open Publication No. 10-2012-004115, as an OPS-producing microorganism, the RhtB protein variant of the present invention was introduced into the microorganism to produce OPS. Also, in the present invention, the OPS-producing strain CA07-0022/pCL-Prmf-serA*(G336V)-serC-rhtB ml comprising the RhtB ml protein variant of the present invention, which is a representative strain having introduced therein the rhtB protein variant having enhanced OPS export activity, was named "Escherichia coli CA07-0227" and deposited with the Korean Culture Center of Microorganisms, recognized as an international depositary authority under the Budapest Treaty, on Mar. 7, 2013 under the accession number KCCM11398P (Example 2).

In addition, the microorganism may further have a reduced ability to perform the intracellular uptake or degradation of OPS.

Specifically, the microorganism may be a microorganism mutated to reduce the activity of PhnC/PhnD/PhnE alkylphosphonate ABC transporter (PhnCDE operon, that is, ATP-binding component of phosphonate transport (PhnC; EG 10713)-periplasmic binding protein component of Pn transporter (PhnD; EG 10714)-integral membrane component of the alkylphosphonate ABC transporter (PhnE; EG 11283)), alkaline phosphatase (PhoA) or acid phosphatase (AphA).

The OPS-producing microorganism of the present invention may further have enhanced activity of pyrimidine nucleotide transhydrogenase (PntAB; EC 1.6.1.1). As previously described in Sauer U P et al., J Biol Chem.20; 279(8):6613-9. Epub 2003, PntAB participates in the metabolism of NADPH to regulate the intracellular redox balance.

A further aspect of the present invention also includes a method for producing OPS, comprising culturing the OPS-producing microorganism.

Herein, the OPS and the OPS-producing microorganism are as described above.

Specifically, the method for producing OPS may comprise the steps of: a) culturing an OPS-producing microorganism comprising the RhtB protein variant to produce OPS; and b) isolating OPS from the culture of the microorganism. Specifically, the method may comprise the steps of: a) culturing an OPS-producing microorganism comprising the RhtB protein variant to produce OPS; and b) isolating OPS from the culture of the microorganism, but is not limited thereto.

The OPS-producing microorganism is specifically a microorganism that has reduced activity of endogenous SerB so as to be able to accumulate OPS therein. In addition, the OPS-producing microorganism may further have enhanced activity of SerA resistant to serine feedback inhibition and/or SerC, and this activity is as described above.

As used herein, the term "culturing" means growing the microorganism under artificially controlled conditions. A culturing process in the present invention may be performed using a suitable medium and culture conditions well known in the art. Any person skilled in the art can readily control the culture process depending on the type of strain selected. Specifically, the culturing may be batch-type culture, continuous culture or fed-batch culture, but is not limited thereto.

In culture of the recombinant microorganism having reduced activity of endogenous SerB, the medium should additionally contain glycine or serine, because the serine auxotrophy of the recombinant microorganism is induced. Glycine may be provided in the form of purified glycine, a glycine-containing yeast extract, or tryptone. The concentration of glycine in the medium is generally 0.1-10 g/L, and specifically 0.5-3 g/L. In addition, serine may be provided in the form of purified serine, a serine-containing yeast extract or tryptone. The concentration of serine in the medium is generally 0.1-5 g/L, and specifically 0.1-1 g/L.

In addition, the medium may contain a carbon source. Examples of the carbon source may include saccharides and carbohydrates such as glucose, sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used alone or in combination in the medium. Examples of a nitrogen source that may be contained in the medium include organic nitrogen sources such as peptone, yeast extract, meat juice, malt extract, corn steep liquor, soybean, and wheat protein, and inorganic nitrogen sources such as urea, ammonium sulfate, ammonium chloride, ammonium phosphate, ammonium carbonate and ammonium nitrate. These nitrogen sources may be used alone or in combination. Examples of a phosphorous source that may be contained in the medium include potassium dihydrogen phosphate, potassium phosphate, and corresponding sodium salts. In addition, the medium may contain metal salts such as magnesium sulfate or iron sulfate. Additionally, the medium may also contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culturing to adjust the pH of the culture medium. In addition, during culturing, a defoaming agent such as fatty acid polyglycol ester may be used to suppress the formation of foam. Further, in order to maintain the culture medium in an aerobic state, oxygen or oxygen-containing gas can be injected into the culture medium. For an anaerobic or microaerobic condition, nitrogen, hydrogen, or carbon dioxide may be provided without aeration. The culture medium may be typically maintained at a temperature ranging from 27° C. to 37° C., and specifically from 30° C. to 35° C. As for the culture period, culture can be continued until desired amounts of useful substances are produced. Specifically, the culture period may be 10-100 hours.

In the present invention, the OPS produced in the culturing step may further be isolated and purified. For example, the desired OPS can be collected from the culture using a suitable method known in the art depending on a culture method, for example, a batch-type culture, continuous culture or fed-batch culture method.

In an example of the present invention, a plasmid comprising each of the four RhtB protein variants was introduced into an OPS-producing strain, and then the strain was cultured and the OPS productivity thereof was examined. As a result, the OPS-producing strain introduced with the plasmid for each of the four protein variants showed an increase in OPS productivity of up to 14% compared to an OPS-producing strain introduced a plasmid with wild-type RhtB (Example 2).

A further aspect of the present invention also includes a method for producing cysteine or its derivatives, the method comprising reacting OPS, produced by the above-described OPS production method, with a sulfide in the presence of O-phosphoserine sulfhydrylase (OPSS) or a microorganism that expresses OPSS.

Specifically, the method for producing cysteine or its derivatives comprises the steps of: a) producing OPS by culturing an OPS-producing microorganism comprising the RhtB protein variant; and b) reacting the OPS, produced in step a), with a sulfide in the presence of O-phosphoserine sulfhydrylase (OPSS) or a microorganism that expresses OPSS, but is not limited thereto. FIG. 1 shows a schematic diagram showing the process for synthesis of cysteine.

Step a) of the method is as described above. In addition, the method of the present invention comprises step b) of reacting the OPS, produced in step a), with a sulfide in the presence of O-phosphoserine sulfhydrylase (OPSS) or a microorganism that expresses OPSS.

The sulfide that is used in the present invention may be any sulfide that may be provided not only in a solid form that is generally used in the art, but also in a liquid or gas form due to the difference in pH, pressure and/or solubility, and may be converted to a thiol (SH) group in the form of, for example, sulfide ($S^{2-}$) or thiosulfate ($S_2O_3^{2-}$). Specifically, the sulfide that is used in the present invention may be $Na_2S$, NaSH, $H_2S$, $(N_4)_2S$, NaSH or $Na_2S_2O_3$, which can provide a thiol group to OPS. In the reaction, a single thiol group is supplied to a single reactive OPS group to produce a single cysteine or a derivative thereof. In this reaction, a sulfide is specifically added in an amount of 0.1-3 moles, and specifically 1-2 moles per mole of OPS. Most specifically, OPS and a sulfide that provides a thiol group are used at a molar ratio of 1:1 in light of economy.

As used herein, the term "O-phosphoserine sulfhydrylase (OPSS)" refers to an enzyme that catalyzes a reaction in which a thiol (SH) group is provided to OPS to convert OPS in cysteine. The enzyme was first found in *Aeropyrum pernix, Mycobacterium tuberculosis, Mycobacterium smegmatics,* and *Trichomonas vaginalis* (Mino K and Ishikawa K, FEBSletters, 551: 133-138, 2003; Burns KE et al., J. Am. Chem. Soc., 127: 11602-11603, 2005). In addition, the scope of OPSS includes not only a wild-type OPSS protein, but also a protein variant that comprises a deletion, substitution or addition in one or more nucleotides of a polynucleotide sequence encoding the OPSS and shows activity that is equal to or higher than the biological activity of wild-type OPSS protein. Further, the scope of OPSS includes the OPSS protein disclosed in Korean Patent Laid-Open Publication No. 10-2012-0041115 and Korean Patent Registration No. 10-1208267, and its protein variants.

In addition, the method of the present invention may further comprise a step of isolating and purifying the cysteine produced by the reaction of step b). Herein, the desired cysteine can be collected by isolating and purifying it from the reaction solution using a suitable reaction known in the art.

Further, the cysteine produced by the method of the present invention can be easily synthesized into a cysteine derivative by a chemical synthesis reaction known in the art.

As used herein, the term "derivatives" refers to similar compounds obtained by chemically modifying a portion of any compound. Usually, the term means compounds in which a hydrogen atom or an atom group substituted with another hydrogen atom or atom group.

As used herein, the term "cysteine derivatives" refers to compounds in which a hydrogen atom or atom group in cysteine is substituted with another atom or atom group. For example, the cysteine derivatives may have a form in which the nitrogen atom of the amine group ($-NH_2$) or the sulfur atom of the thiol group ($-SH$) in cysteine has another atom or atom group attached thereto. Examples of cysteine derivatives include, but are not limited to, NAC (N-acetylcysteine), SCMC (S-carboxymetylcysteine), BOC-CYS(ME)-OH, (R)—S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-cys(Boc-methyl)-OH, seleno-L-cystine, S-(2-thiazolyl)-L-cysteine, S-(2-thienyl)-L-cysteine, S-(4-tolyl)-L-cysteine, etc. Cysteine can be easily synthesized into NAC (N-acetylcysteine) by reaction with an acetylation agent, and in basic conditions, it can be synthesized into SCMC (S-carboxymetylcysteine) by reaction with haloacetic acid. These cysteine derivatives are used mainly as pharmaceutical materials, including cough remedies, cough-relieving agents, and therapeutic agents for bronchitis, bronchial asthma and sore throat.

Hereinafter, the present invention will be described in further detail with reference to examples. It is to be understood, however, that these examples are for illustrative purposes only and are not intended to limit the scope of the present invention.

EXAMPLE 1

Identification of RhtB (homoserine/homoserine lactone Export Transporter) Protein Variants In order to increase the specificity of an O-phosphoserine (OPS) exporter to increase the OPS-secreting ability of an OPS-producing strain, the present inventors constructed RhtB protein variants, which are OPS exporters, in the following manner.

Specifically, to construct protein variants, the rhtB open reading frame was amplified by random mutagenesis PCR (JENA error-prone PCR) using the genomic DNA of *Escherichia coli* K12_W3110, ATCC 27325) as a template and a gene-specific primer pair. Each of the gene fragments obtained by the PCR was cleaved with EcoRV and HindIII and cloned into a pCL Prmf vector comprising an rmf promoter inserted into a pCL1920 vector (GenBank No AB236930). Herein, the amplification of the rhtB gene was performed using primers of SEQ ID NOS: 8 and 9.

The recombinant plasmid libraries constructed by the above-described process were subjected to high-throughput screening (HTS). A platform strain for the screening was a recombinant microorganism mutated to reduce the activity of endogenous phosphoserine phosphatase (SerB) in the wild-type *E. coli* strain W3110 and was named "CA07-0012" (KCCM11212P; Korean Patent Laid-Open Publication No. 10-2012-0041115).

To identify mutants having increased OPS export activity, the constructed plasmid libraries were transformed into CA07-0012 by electroporation, and then colonies showing the removal of growth inhibition under medium conditions containing an excessive amount of OPS were selected. Plasmids were obtained from the selected colonies, and the nucleotide sequences thereof were analyzed by a sequencing technique.

As a result, the following four RhtB protein variants involved in removing growth inhibition under medium conditions containing an excessive amount of OPS were selected: an RhtB protein variant having an amino acid sequence of SEQ ID NO: 2 and named "RhtB m1"; an RhtB protein variant having an amino acid sequence of SEQ ID NO: 3 and named "RhtB m2"; an RhtB protein variant having an amino acid sequence of SEQ ID NO: 4 and named "RhtB m3"; and an RhtB protein variant having an amino acid sequence of SEQ ID NO: 5 and named "RhtB m4".

EXAMPLE 2

Examination of OPS Export Activities of rhtB Protein Variants in OPS-Producing Strain A plasmid comprising each of the four protein variants identified in Example 1 was introduced into the OPS-producing strain CA07-0012, and then the O-phosphoserine productivities of the resulting strains were evaluated.

Specifically, each of the strains was plated on LB solid medium and cultured overnight in an incubator at 33° C. Each of the strains cultured overnight on the LB solid medium was inoculated into a 25-mL titer medium shown in Table 1 below, and was then incubated in an cultured at a temperature of 34.5° C. and 200 rpm for 48 hours. The results of the culture are shown in Table 2 below.

TABLE 1

| Composition | Concentration (per liter) |
| --- | --- |
| Glucose | 50 g |
| $KH_2PO_4$ | 6 g |
| $(NH_4)_2SO_4$ | 17 g |
| $MgSO_4 \cdot 7H_2O$ | 1 g |
| $FeSO_4 \cdot 7H_2O$ | 5 mg |
| $MnSO_4 \cdot 4H_2O$ | 10 mg |
| L-glycine | 2.5 g |
| Yeast extract | 3 g |
| Calcium phosphate | 30 g |
| pH | 6.8 |

TABLE 2

| Name of strain | OD562 nm | Consumption of glucose (g/L) | O-phosphoserine (g/L) |
| --- | --- | --- | --- |
| CA07-0012/pCL-Prmf-rhtB(wt) | 40 | 35 | 1.5 |
| CA07-0012/pCL-Prmf-rhtB m1 | 37 | 35 | 1.7 |
| CA07-0012/pCL-Prmf-rhtB m2 | 41 | 34 | 1.8 |

TABLE 2-continued

| Name of strain | OD562 nm | Consumption of glucose (g/L) | O-phosphoserine (g/L) |
| --- | --- | --- | --- |
| CA07-0012/pCL-Prmf-rhtB m3 | 38 | 35 | 1.8 |
| CA07-0012/pCL-Prmf-rhtB m4 | 37 | 35 | 1.8 |

As can be seen in Table 2 above, the strains with the rhtB protein variants of the present invention showed excellent results corresponding to an increase in OPS production of up to 10% compared to a strain introduced with wild-type rhtB gene.

In order to verify the activities of the rhtB protein variants of the present invention, the strain CA07-0022/pCL-Prmf-serA*(G336V)-serf (KCCM11103P; Korean Patent Laid-Open Publication No. 10-2012-0041115) having enhanced activities of SerA (D-3-phosphoglycerate dehydrogenase) and SerC (3-phosphoserine aminotransferase), which are involved in the biosynthesis pathway of OPS, was used as an OPS-producing strain having an increased ability to produce OPS. To construct a pCL-Prmf-serA(G336V)-serC_Prmf-genes vector, the pCL-PrhtB-genes vector was amplified using primers of SEQ ID NOS: 6 and 7.

Specifically, each of the strains was plated on LB solid medium and cultured overnight in an incubator at 33° C. Each of the strains cultured overnight on the LB solid medium was inoculated into a 25-mL titer medium shown in Table 1 below, and was then incubated in an cultured at a temperature of 34.5° C. and 200 rpm for 48 hours. The results of the culture are shown in Table 3 below.

TABLE 3

| Name of strain | OD562 nm | Consumption of glucose (g/L) | O-phosph-oserine (g/L) |
| --- | --- | --- | --- |
| CA07-0022/pCL Prmf serA*C-Prmf-rhtB(wt) | 43 | 33 | 2.5 |
| CA07-0022/pCL Prmf serA*C-Prmf-rhtB m1 | 41 | 31 | 2.6 |
| CA07-0022/pCL Prmf serA*C-Prmf-rhtB m2 | 42 | 31 | 2.6 |
| CA07-0022/pCL Prmf serA*C-Prmf-rhtB m3 | 42 | 32 | 3.0 |
| CA07-0022/pCL Prmf serA*C-Prmf-rhtB m4 | 41 | 31 | 2.6 |

As can be seen in Table 3 above, when the rhtB protein variants of the present invention were introduced into the OPS-producing strain having an enhanced ability to produce OPS, the production of OPS in the strain was increased by up to 14%, suggesting that the rhtB protein variants of the present invention are useful for the production of OPS.

In addition, the strain CA07-0022/pCL Prmf serA*C-Prmf-rhtB m1 that is a typical strain introduced with the rhtB protein variant having enhanced OPS export activity was named "*Escherichia coli* CA07-0227" and deposited with the Korean Culture Center of Microorganisms, recognized as an international depositary authority under the Budapest Treaty, on Mar. 7, 2013 under the accession number KCCM11398P.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method or producing cysteine or its derivatives, comprising the steps:
   a) culturing a microorganism which comprises a vector comprising a polynucleotide encoding RhtB (homoserine lactone export transporter) protein variant having an amino acid sequence of SEQ ID NO: 2,3,4, or 5 to produce 0- phosphoserine (OPS); and
   b) reacting the OPS, produced in step a), with a sulfide in the presence of 0- phosphoserine sulfhydrylase (OPSS) or a microorganism that expresses OPSS to produce cysteine or its derivatives.

2. The method according to claim 1, wherein the microorganism further has reduced activity of endogenous phosphoserine phosphatase (SerB) or enhanced activity of phosphoserine aminotransferase (SerC) or phosphoglycerate dehydrogenase (SerA) resistant to serine feedback inhibition, or the RhtB protein variant.

3. The method according to claim 1, wherein the sulfide is one or more selected from the group consisting of $Na_2S$, NaSH, $(NH_4)_2S$, $H_2S$ and $Na_2S_2O_3$.

4. The method according to claim 2, wherein the sulfide is one or more selected from the group consisting of $Na_2S$, NaSH, $(NH_4)_2S$, $H_2S$ and $Na_2S_2O_3$.

* * * * *